United States Patent [19]

Kobel, deceased et al.

[11] 4,142,943

[45] Mar. 6, 1979

[54] METHOD FOR PURIFYING PENTACHLOROPHENOL

[75] Inventors: Erwin H. Kobel, deceased, late of Midland, Mich., by Elfreda Kobel, administratrix; Masao Yoshimine, Midland, Mich.

[73] Assignee: The Dow Chemical Company, Midland, Mich.

[21] Appl. No.: 508,367

[22] Filed: Sep. 23, 1974

[51] Int. Cl.$^2$ .................. B01D 3/34; C07C 37/22; C07C 39/24
[52] U.S. Cl. .................................... 203/6; 203/38; 203/64; 568/755
[58] Field of Search ................... 203/64, 38, 65, 6; 260/623 R, 627 G, 624 A; 568/755

[56] References Cited

U.S. PATENT DOCUMENTS

| | | | |
|---|---|---|---|
| 3,646,225 | 2/1972 | Morrison | 260/623 R |
| 3,655,523 | 4/1972 | Seeburger et al. | 203/64 X |
| 3,692,561 | 9/1972 | Hager | 260/623 R X |
| 3,816,268 | 6/1974 | Watson et al. | 203/38 |
| 3,830,708 | 8/1974 | Karhan et al. | 203/64 |
| 3,909,365 | 9/1975 | Christena | 203/6 |
| 4,016,047 | 4/1977 | Christena | 203/6 |

*Primary Examiner*—Joseph Scovronek
*Attorney, Agent, or Firm*—G. R. Baker

[57] ABSTRACT

The decomposition of pentachlorophenol during distillation to remove impurities is markedly reduced by incorporating into the distilling molten pentachlorophenol a hydroxyl or polyhydroxyl containing organic compound having a boiling point above about 100° C. in the presence or absence of water.

10 Claims, No Drawings

METHOD FOR PURIFYING PENTACHLOROPHENOL

BACKGROUND OF THE INVENTION

Pentachlorophenol is a useful antimicrobial agent which has been found to decompose readily in the presence of metals and metal chlorides and heat. In addition the by-products of the method of manufacture, as well as the metal and heat produced decomposition products are undesirable both from the aesthetic viewpoint and the environmental viewpoint. Pentachlorophenol without these by-products and/or decomposition products is substantially environmentally satisfactory.

Therefore, it would be advantageous to provide an inhibitor for crude pentachlorophenol which will permit the pentachlorophenol to be distilled from its by-products and simultaneously reduce, if not substantially eliminate, the decomposition during distillation of these by-products and/or the pentachlorophenol.

BRIEF DESCRIPTION OF THE INVENTION

In accordance with the present invention crude pentachlorophenol, prepared for example in the presence of a Friedel Crafts catalyst such as aluminum chloride ($AlCl_3$), can be effectively distilled in a metal still by adding to the crude pentachlorophenol a hydroxyl or polyhydroxyl containing hydrocarbon compound which may contain a plurality of ether linkages. Good results have been obtained when from about 0.1 to about 10 percent by weight and preferably from about 0.3 to 3 percent by weight hydroxyl compound, based upon the weight of the crude pentachlorophenol, is added to the crude pentachlorophenol during distillation. The hydroxyl containing compound may be anhydrous or may contain water, i.e. 0 to 90% aqueous solutions. In some instances for reasons yet unknown, better results are achieved when water is present.

The class of hydroxyl hydrocarbon compounds which are suitable for use in accordance with the present invention are:

a. the sugars
b. the polyhydric alcohols
c. polyglycols
d. ethers of polyglycols
e. mixtures of the above with water.

Exemplary of the compounds within the enumerated classes are sorbitol, ethylene glycol, propylene glycol, pentaerythritol, tetraethylene glycol, polyethylene glycols of molecular weights 200 to 400, polyglycerol, polyol 80 (80% glycerine ca 20% dimethylol dioxanes) and the like.

DETAILED DESCRIPTION OF THE INVENTION

A 500 ml distillation flask was prepared containing 28.9 gms nickel having a surface area of 132 $in^2$, 2.48 gms 316 stainless steel also having a surface area of 132 $in^2$ and 0.45 gms iron having a surface area of 1.32 $in^2$. To such prepared flask was added 500 gms of commercial pentachlorophenol prills and 2 gms polyethylene glycol having an average molecular weight of 200. The pentachlorophenol was melted at 200° C. and distilled at 75 mm Hg through a 1" × 7" column packed with 0.16 inch 316 stainless steel protruded packing plus 0.7 gms (2.9 $in^2$) iron protruded packing. The distillation took one hour. There was collected 439.5 gms (87.9% of the pentachlorophenol 500 gms feed. The decomposition of the pentachlorophenol was followed by scrubbing the exit gas from the pump with 1 N NaOH and back-titrating with HCl. The residue, 60.5 gms was heated to 270° C. for 4 hours to simulate plant conditions in a reboiler under extreme temperature conditions. The decomposition of the residue was followed by scrubbing the exit gas with 1 N NaOH and back-titrating with HCl. The residue on heating for 4 hours at 270° C. decomposed but much less rapidly than uninhibited pentachlorophenol.

In a similar manner other hydroxyl containing hydrocarbons were tested. The results are set forth below. The grade of pentachlorophenol employed is identified by the superscript-footnote notations.

TABLE I
Stabilization of Pentachlorophenol to Distillation
Initial Pentachlorophenol Charge, 1.87 moles

| Inhibitor | HCl Evolution, m moles[5] Distillation | Residue held at 270° C, 4 hrs. | Residue % | Overhead Yield, % |
|---|---|---|---|---|
| None[1] | 320 | 181 | 38.8 | 56.4 |
| .4% Pentaerythritol (PE)[1] | 2.0 | 46.7 | 11.1 | 89.8 |
| .4% 4/6 PE/$H_2O$[1] | 1.5 | 14.7 | 11.9 | 87.3 |
| .4% Sorbitol[1] | 2.1 | 56.9 | 10.7 | 88.5 |
| .4% Tetraethylene glycol (TEG)[1] | 1.5 | 35.7 | 11.5 | 87.5 |
| .4% 3/1 TEG/$H_2O$[1] | 1.9 | 44.3 | 9.3 | 90.0 |
| .4% 2/1 TEG/$H_2O$[1] | 3.0 | 42.5 | 10.6 | 88.7 |
| .4% 1/1 TEG/$H_2O$[1] | 1.7 | 5.0 | 11.9 | 87.7 |
| .4% Ethylene glycol (EG)[1] | 1.8 | 25.8 | 12.0 | 86.9 |
| .4% 1/1 EG/$H_2O$[1] | 1.9 | 25.8 | 10.9 | 88.4 |
| .4% 1/2 EG/$H_2O$[1] | 1.9 | 3.4 | 9.6 | 89.7 |
| .4% Polyethylene glycol (MW-400)[1,a] | 4.0 | 48.1 | 12.2 | 87.0 |
| .4% Polyethylene glycol (MW-200)[1,b] | 2.1 | 32.0 | 11.4 | 87.9 |
| .4% Polyethylene glycol (MW-200)[1,b] | 2.3 | 8.7 | 12.0 | 86.9 |
| None | 100.5 | 44.1 | 15.8 | 83.6 |
| .4% E-200-hu 2,b | 2.0 | 29.4 | 10.2 | 89.1 |
| .8% E-200[2,b] | 2.7 | 49.9 | 10.5 | 89.4 |
| .3% E-200[2,b] | 14.9 | 38.6 | 12.0 | 87.6 |
| .4% 1/1 Polyglycerine[c]/$H_2O_3$ | 2.5 | 27.9 | 8.1 | 91.1 |
| .4% 1/1 SAT/$H_2O$[3,4] | 3.0 | 11.1 | 11.9 | 88.6 |
| .4% 1/1 Polyol 80/$H_2O$[3,d] | 2.2 | 10.6 | 10.0 | 89.5 |
| .4% 1/1 EG/$H_2O^3$ | 2.0 | 8.0 | 8.3 | 91.2 |
| .4% 1/1 Propylene glycol/$H_2O^3$ | 2.2 | 15.2 | 8.3 | 91.0 |
| .4% 1/1 glycerine/$H_2O^3$ | 2.7 | 45.7 | 9.2 | 89.0 |

[1] Commercial pentachlorophenol, .07% $H_2O$
[2] Commercial pentachlorophenol, .008% $H_2O$
[3] Assumed quality of commercial pentachlorophenol similar to that employed under footnote 2
[4] SAT, Salicylaldehyde Waste Tars
[5] Measure of pentachlorophenol decomposition and formation of high molecular weight material.
[a] Polyethylene glycol of an average M.W. 400
[b] Polyethylene glycol of an average M.W. 200
[c] Polyglycerine is a low molecular polymer of glycerine obtained as bottoms from a glycerine still
[d] Polyol 80 (80% glycerine ca 20% dimethylol dioxanes)

What is claimed is:

1. In a process for purifying pentachlorophenol by distilling the pentachlorophenol at from about 190° C. to about 270° C. under subatmospheric pressure the improvement which consists of conducting the distillation in the presence of about 0.1 to about 10 weight percent, based upon the weight of the crude pentachlorophenol, of a hydroxyl containing compound selected from the group consisting of sugars, polyhydric alcohols, ethers of polyglycols and polyglycols, wherein said hydroxyl containing compound is present in a 0 to about 90 percent aqueous solution.

2. The process of claim 1 wherein said hydroxyl compound is ethylene glycol.

3. The process of claim 1 wherein said hydroxyl compound is propylene glycol.

4. The process of claim 1 wherein said hydroxyl compound is glycerine.

5. The process of claim 1 wherein said hydroxyl compound is pentaerythritol.

6. The process of claim 1 wherein said hydroxyl compound is tetraethylene glycol.

7. The process of claim 1 wherein said hydroxyl compound is polyethylene glycol having a molecular weight of about 200.

8. The process of claim 1 wherein said hydroxyl compound is polyethylene glycol having a molecular weight of about 400.

9. The process of claim 1 wherein said hydroxyl compound is polyglycerol.

10. The process of claim 1 wherein said hydroxyl compound is sorbitol.

* * * * *

UNITED STATES PATENT AND TRADEMARK OFFICE
CERTIFICATE OF CORRECTION

PATENT NO. : 4,142,943
DATED : March 6, 1979
INVENTOR(S) : Erwin H. Kobel, deceased, by Elfreda Kobel, administratrix, et al It is certified that error appears in the above–identified patent and that said Letters Patent are hereby corrected as shown below:

Col. 1, line 50; change "to" to --and--.

Col. 2, line 16 of Table I; change "glycol (MW-400)$^{1,a}$" to --glycol (MW-400)$^{1,b}$--.

Col. 2, line 20 of Table I; change "glycol (MW-200)$^{1,b}$" to --glycol (MW-200)$^{1,a}$--.

Col. 2, line 22 of Table I; change ".4% E-200-bu 2,b" to --.4% E-200$^{2,b}$--.

Col. 2, line 26 of Table I; change "/H$_2$O$_3$" to --/H$_2$O$^3$--.

Signed and Sealed this

Tenth Day of July 1979

[SEAL]

Attest:

Attesting Officer

LUTRELLE F. PARKER
Acting Commissioner of Patents and Trademarks